Figure 1:
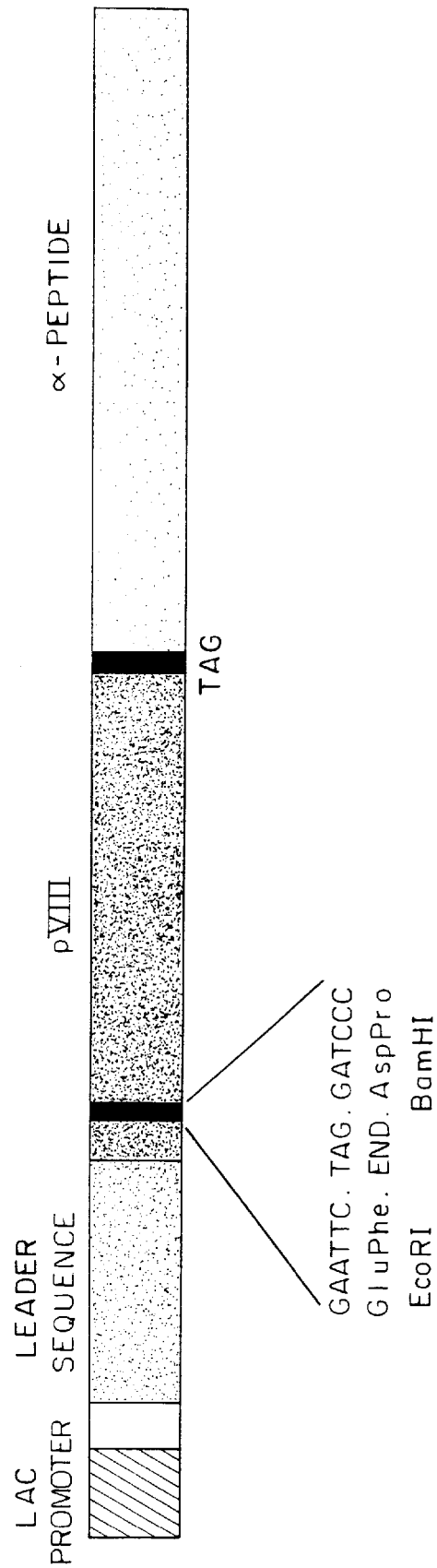

United States Patent [19]

Felici et al.

[11] Patent Number: 5,994,083
[45] Date of Patent: Nov. 30, 1999

[54] PROCESS FOR THE PREPARATION OF IMMUNOGENS OR DIAGNOSTIC REAGENTS, AND IMMUNOGENS OR DIAGNOSTIC REAGENTS THEREBY OBTAINABLE

[75] Inventors: Franco Felici; Alessandra Luzzago; Paolo Monaci; Alfredo Nicosia; Riccardo Cortese, all of Rome, Italy

[73] Assignee: Istituto di Recerche di Biologia Molecolare P. Angeletti S.p.A., Pomezia, Italy

[21] Appl. No.: 08/553,257

[22] PCT Filed: May 5, 1994

[86] PCT No.: PCT/IT94/00054

§ 371 Date: Nov. 13, 1995

§ 102(e) Date: Nov. 13, 1995

[87] PCT Pub. No.: WO94/26886

PCT Pub. Date: Nov. 24, 1994

[30] Foreign Application Priority Data

May 11, 1993 [IT] Italy ................................. RM93A0301

[51] Int. Cl.$^6$ .................. G01N 33/53; G01N 33/566; G01N 33/537
[52] U.S. Cl. .................. 435/7.1; 435/5; 435/6; 435/71; 435/69.1; 435/172.3; 435/239; 436/501; 436/538; 436/811; 935/80
[58] Field of Search ................ 435/172.3, 5, 6, 435/69.1, 7.1, 77.1, 239; 935/50; 436/501, 538, 811

[56] References Cited

U.S. PATENT DOCUMENTS

| | | | |
|---|---|---|---|
| 4,751,181 | 6/1988 | Keene et al. | 435/70 |
| 5,010,175 | 4/1991 | Rutter et al. | . |
| 5,182,366 | 1/1993 | Huebner et al. | . |
| 5,223,409 | 6/1993 | Ladner et al. | . |
| 5,270,170 | 12/1993 | Schatz et al. | 435/7.37 |
| 5,432,018 | 7/1995 | Dower et al. | 435/5 |
| 5,492,807 | 2/1996 | Santi et al. | 435/5 |

FOREIGN PATENT DOCUMENTS

WO 86/00991  2/1986  WIPO .
WO 86/06487  11/1986  WIPO .

OTHER PUBLICATIONS

Barbas et al, "Assembly of combinatorial antibody libraries on phage surfaces: The gene II site", *Proc. Nat. Acad. Sci. USA*, 88:7978–7982 (1991).
Brown, S., "Engineered iron oxide–adhesion mutants of *Escherichia coli* phage λ receptor", *Proc. Natl. Acad. Sci. USA*, 89:8651–8655 (1992).
Christian et al, "Simplified Methods for Construction, Assessment and Rapid Screening of Peptide Libraries in Bacteriophage", *J. Mol. Biol.*, 227:711–718 (1992).
Folgori et al, "A General Strategy to Identify Mimotopes for Pathological Antigene Using Only Random Peptide Libraries and Human Sera", *The EMBO Journal*, 13:2236–2243 (1994).
Geysen et al, "Use of peptide synthesis to probe viral antigens for epitopes to a resolution of a single amino acid", *Proc. Natl. Acad. Sci. USA*, 81:3998–4002 (1984).
Houghten, R., "General method for the rapid solid–phase synthesis of large numbers of peptides: Specificity of antigen–antibody interaction at the level of individual amino acids", *Proc. Natl. Acad. Sci. USA*, 82:5131–5135 (1985).
Lam et al, "A new type of synthetic peptide library for identifying ligand–binding activity", Nature, 354:82–84 (1991).
Dybwad et al, "Structural Characterization of Peptides That Bind Synovial Fluid Antibodies from RA Patients: A Novel Strategy for Identification of Disease–Related Epitopes Using a Random Peptide Library", *Clinical Immunology and Immunopathology*, vol. 75, No. 1, pp. 45–50, Apr. 1995.
Edington, S.M., "Shape Space: Is biopharmaceutical discovery entering a new evolutionary stage?", *Bio/Technology*, vol. 11, pp. 285–289, Mar. 11, 1993.
Devlin et al. Jul. 1990 Science 249 pp. 404–406.
Dybwad et al. Apr. 1993 Eur J Immunol. 23 pp. 3189–3193.
Felici et al. Nov. 1991 J Mol. Biol. 222 pp,. 301–310.
Greenwood et al. Mar. 1991 J Mol Biol 220 pp. 821–827.
Parmley et al. Jan. 1989 Adv. Exp. Med. Biol. pp. 215–218.
Scott et al. Jul. 1992 TIBS 17 pp. 241–245.
Smith et al. Jan. 1993 Methods in Enzymology 217 pp. 228–256.
Scott and Smith Jul. 22, 1990 Science v 249 p. 386.

*Primary Examiner*—Frank C. Eisenschenk
*Assistant Examiner*—Mary K Zeman
*Attorney, Agent, or Firm*—Browdy and Neimark

[57] ABSTRACT

A process for the preparation of immunogens or diagnostic reagents that mimic an antigen or a pathogenic organism specific to a disease, essentially characterized by the following operations: identification of at least one antibody that reacts with the antigen or pathogenic organism specific to the disease; construction of phage libraries which display on the surface of the capsid oligopeptides, expressed from random sequence oligonucleotidic inserts introduced into a gene coding for a phage capsid protein using genetic manipulation techniques (for example using a plasmid engineered for the purposes of the invention, the genetic map of which is shown in the figure); selection of the phages that display on the surfaces of the capsid antigenic oligopeptides recognized by said antibody; optional use of the selected phages and/or fragments thereof and/or their derivatives for the formulation of diagnostic kits for the specific pathogenic agent, or in general for the diseases, including immunological disorders typical of so-called autoimmune diseases, with known or unknown etiology and/or pathogenesis; optional use of the selected phages and/or fragments thereof and/or their derivatives for the formulation of an antagonist ofthe antigen-antibody reactions for treatment of the disease induced by said antigen; optional use of the selected phages and/or fragments thereof and/or their derivatives to induce a tolerance of the phenomena of hypersensitivity and/or allergy to compounds and/or natural or synthetic preparations; optional immunization of an organism by means of the selected phages and/or fragments thereof and/or their derivatives; and optional verification of the presence, in the serum of the immunized organism, of antibodies that recognize the above antigen or organism specific to the disease.

8 Claims, 1 Drawing Sheet

PROCESS FOR THE PREPARATION OF IMMUNOGENS OR DIAGNOSTIC REAGENTS, AND IMMUNOGENS OR DIAGNOSTIC REAGENTS THEREBY OBTAINABLE

DESCRIPTION

The subject of the present invention is a process for the preparation of immunogens or diagnostic reagents that mimic an antigen or a pathogenic organism specific to a disease, even if this is uncharacterized or even unknown (thereby including auto-immune diseases whose etiology and/or pathogenesis is known or unknown). This process is based on the existence and availability of antibodies, both monoclonal or polyclonal, or of serum containing antibodies, which react specifically with the organism causing the infection.

Antibodies suitable for use in this process can be specific for any antigen of interest for which an immunogen or diagnostic reagent that mimes the antigen is sought. The antigen can be a protein or peptide whether synthetic, derived from a natural source, or produced recombinantly; carbohydrate; polysaccharide; glycoprotein; hormone; receptor; antibody; virus; substrate; metabolite; transition state analog; cofactor; drug; dye; nutrient; growth factor; cellular component; oncogene product; bacteria and their extracellular products; mammalian cells and extracts therefrom including tumor cells, virus infected cells and normal cells; parasites; protozoa; malarial antigens; helminths; fungi; rickettsia; or an allergen including but not limited to pollens, dusts, danders or extracts of the same; or a venom, poison, toxin, or toxoid; nucleic acids including DNA; or any other antigen without limitation. Antigens of viruses which are suitable for use in the present invention include antigens from the viruses including but not limited to polio virus, influenza virus, HIV, HTLL, papilloma virus, adeno virus, parainfluenza virus, measles virus, mumps virus, respiratory syncytial virus, shipping fever virus, Western and Eastern encephalomyelitis virus, Japanese B encephalomyelitis virus, Russian spring-summer encephalomyelitis virus, hog cholera virus, hepatitis virus, pox virus, rabies, virus, distemper virus, herpes virus, cytomegalo virus, foot and mouth disease virus, rhinovirus, Newcastle disease virus, vaccinia virus; and pseudorabies virus. The mime can be an immunogen, a vaccine, an inhibitor or activator, etc. without limitation.

As is known, all vaccines and diagnostic reagents currently on sale or undergoing clinical tests are conventionally obtained by means of processes based on the manipulation, modification and/or adaptation of pathogenic organisms or components thereof. These methods have given good results, but are not without problems. The greatest limitation associated with these methods is connected with the fact that they depend upon the availability of information and/or material directly deriving from pathogenic organisms or components thereof.

Previous attempts to overcome the above described limitation have so far failed for a lack of an efficient and reproducible experimental protocol; in particular, these attempts did not provide sufficient information in order to identify and characterize immunogenic mimics to be used for diagnosis and vaccine therapy. It must be emphasized that the present invention is focused on the development of a new technology aimed at overcoming conceptual and technical inadequancies of previously proposed protocols.

A key feature of the present invention is a novel strategy for the selection of antigenic and immunogenic mimics, based on the use, as reagents, of serum samples from patients and a counter-selection step utilizing serum samples from healthy individuals.

Use of the process for preparation according to the present invention allows this limitation to be overcome, furthermore offering additional advantages which will be clear from the following description.

The process for the preparation of immunogens or diagnostic reagents that mimic an antigen or a pathogenic organism specific to a disease—according to the present invention—is essentially characterized by the following operations:

identification of at least one antibody that reacts with the antigen or pathogenic organism specific to the disease;

construction of phage libraries which display on the surface of the capsid oligopeptides, expressed from random sequence oligonucleotidic inserts introduced into a gene coding for the phage capsid using genetic manipulation techniques;

selection of the phages that display on the surfaces of the capsid antigenic oligopeptides with a first pathologic serum, subsequent screening with additional pathological sera in order to identify phage that display oligopeptides that react with all or most of the sera tested, and counterscreening with a panel of sera from another set of individuals taken as a control in order to identify oligopeptides that do not react with all or most sera from controlled individuals;

optional use of the selected phages and/or fragments thereof and/or their derivatives for the formulation of diagnostic kits for the specific pathogenic agent, or in general for the diseases, including immunological disorders typical of so-called autoimmune diseases, with known or unknown etiology and/or pathogenesis;

optional use of the selected phages and/or fragments thereof and/or their derivatives for the formulation of an antagonist of the antigen-antibody reactions for treatment of the disease induced by said antigen;

optional use of the selected phages and/or fragments thereof and/or their derivatives to induce a tolerance of the phenomena of hypersensitivity and/or allergy to compounds and/or natural or synthetic preparations;

optional immunization of an organism by means of the selected phages and/or fragments thereof and/or their derivatives; and optional verification of the presence, in the serum of the immunized organism, of antibodies that recognize the above antigen or organism specific to the disease.

The construction of phage libraries, according to the present invention, can be advantageously performed using the filamentous phages M13, F1 and Fd, or derivatives thereof. The reasons for this are the following:

filamentous phages are commonly used as molecular vectors in the field of molecular biology and genetic engineering. For example, by taking advantage of their feature to contain a genome with a single DNA helix, they have been particularly used in DNA sequencing experiments, in direct site mutagenesis experiments and for the expression of proteins and peptides;

the information required and sufficient for encapsidation of a single chain DNA genome has been well characterized and can be transferred to other molecular vectors;

it has likewise been demonstrated that at least two proteins of the capsid of filamentous phages can be modified by means of the addition or insertion of additional amino acid sequences. The resulting phages are encapsidated, maintain their ability to replicate and, in most cases, to infect bacterial cells. The foreign amino acid sequences are displayed on the surface of the phage, and can be recognized by interaction with antibodies or with other specific molecules according to the case.

The antibodies that can be used in the process for the preparation of immunogens and diagnostic reagents according to the present invention can be monoclonal antibodies, polyclonal antibodies, or antibodies contained in sera. The latter form of embodiment is of particular interest, because it provides for the first time a reproducible experimental strategy to identify novel antigenic and immunogenic mimics in absence of any information on the structure and properties of the natural and pathological antigen.

The gene coding for the phage capsid, with random sequence oligonucleotidic inserts, can be the gene coding for the protein VIII of the phage capsid or the gene coding for the protein III of said capsid.

The process according to the invention can be applied without restriction to any antibody or organism responsible for illness. Good results have been obtained using monoclonal antibodies, or sera specific for the surface antigen of the human hepatitis B virus (HBsAg).

The antigenic oligopeptides recognized by the antibodies used can be obtained by expression from random sequence oligonucleotidic inserts, using as a vector, for example, the plasmid pC89.

In the process for the preparation of immunogens and diagnostic reagents according to the present invention, it is possible to select phages containing in their capsid from the site identifying the restriction enzyme EcoRI (GAATTC) to that identifying the restriction enzyme BamHI (GGATCC), one of the aminoacidic sequences SEQ ID NO: 1, SEQ ID NO: 2, SEQ ID NO: 3, SEQ ID NO:7 and SEQ ID NO: 9 to 47.

The present invention is not limited to the process for the preparation of immunogens or diagnostic reagents against a specific pathogenic agent, but also extends to the immunogens and diagnostic reagents obtainable using the process illustrated above, and to the phages usable in the process mentioned above.

Furthermore, the invention also extends to the plasmids pC89 containing, wholly or in part, a nucleotidic sequence chosen from the group comprising the sequences SEQ ID NO: 4, SEQ ID NO: 5, SEQ ID NO: 6 and SEQ ID NO:8.

The present invention refers also to oligopeptides obtainable by the above process which react with pathological sera from individuals affected by the same disease affecting the patients whose sera have been used for the selection and screening of phage displaying said oligopeptides and which do not react with sera from individual not affected by the same disease. The above oligopeptides are capable of eliciting in a living organism an immune response against the natural antigens or antibodies against HCV or antibodies against HBV.

Subject matter of the present invention is also the use of the above oligopeptides as immunogens to elicit an antibody response against specific pathological antigens, such as for instance infectious pathogens, in the case said elicited antibodies also being protective or neutralizing, to formulate a vaccine against said pathogenic agents.

The immunogens obtained from the process of the present invention are useful as vaccines or immunizing agents as well as being useful as diagnostic reagents. The vaccines or immunizing agents are administered to a patient in need of such treatment according to standard methods known in the art. The vaccine or immunizing agents can be administered and used either singly or in combination. The vaccines and immunogens of the present invention can comprise the phage or protein and peptides isolated therefrom.

Kits containing the immunogens obtained from the process of the present invention may be prepared. Such kits are used to detect the presence of the antigen in a sample. Such characterization is useful for a variety of purposes including but not limited to forensic analyses and epidemiological studies. Such a kit would comprise a compartmentalized carrier suitable to hold in close confinement at least one container. The carrier would further comprise reagents such as the immunogens, and antibodies suitable for detecting the antigens. The carrier may also contain a means for detection such as labeled antigen or enzyme substrates or the like.

Pharmaceutically useful compositions comprising the immunogens and vaccines of the present invention, may be formulated according to known methods such as by the admixture of a pharmaceutically acceptable carrier. Examples of such carriers and methods of formulation may be found in Remington's Pharmaceutical Sciences. To form a pharmaceutically acceptable compositions suitable for effective administration, such compositions will contain an effective amount of the vaccine or immunogen of the present invention.

Therapeutic or diagnostic compositions of the invention are administered to an individual in amounts sufficient to treat or diagnose the relevant disorders. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The present invention also has the objective of providing suitable topical, oral systemic and parenteral pharmaceutical formulations for use in the novel methods of treatment of the present invention. The compositions containing vaccine or immunogens identified according to this invention as the active ingredient can be administered in a wide variety of therapeutic dosage forms in conventional vehicles for administration. For example, the vaccines and immunogens can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraderitoneal, subcutaneous, topical with or without occlusion, or intramuscular form, all using forms well known to those of ordinary skill in the pharmaceutical arts. An effective but non-toxic amount of the vaccines and immunogens can be employed.

The daily dosage of the vaccines and immunogens may be varied over a wide range from 0.01 to 1000 mg per adult human/per day. For oral administration, the vaccines and immunogens are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the vaccines and immunogens is ordinarily supplied at a dosage level of from about 0.0001 mg/kg to about 100 mg/kg of body weight per day. The range is more particularly from about 0.001 mg/kg to 10 mg/kg of body weight per day. The dosages of the vaccines and immunogens are adjusted when combined to achieve desired effects. On the other hand, dosages of these various agents may be independently optimized and combined to achieve a synergistic result wherein the pathology is reduced more than it would be if either agent were used alone.

Advantageously, vaccine or immunogens of the present invention may be administered in a single dose, or a single daily dose, or the total daily dosage may be administered in divided doses of two, three or four times daily. Furthermore, vaccine or immunogens for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the vaccine or immunogens of the present invention is selected in accordance with a variety of factors including type, species, age, weight, sex and medical condition of the patient; the severity of the condition to be treated; the route of administration; the renal and hepatic function of the patient; and the particular vaccine or immunogen thereof employed. A physician or veterinarian of ordinary skill can readily determine and prescribe the effective amount of the vaccine or immunogens of the present invention required to prevent, counter or arrest the progress of the condition. Optimal precision in achieving concentrations of the vaccine or immunogens of the present invention within the range that yields efficacy without toxicity requires a regimen based on the kinetics of the vaccine or immunogens of the present invention availibility to target sites. This involves a consideration of the distribution, equilibrium, and elimination of the vaccine or immunogens of the present invention.

In the methods of the present invention, the vaccine or immunogens herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active vaccine or immunogen component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methylcellulose, agar bentonite, xanthan gum and the like.

For liquid forms the active vaccine or immunogen component can be combined in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active vaccine or immunogen component can be admixed with a variety of carrier materials well known in the art, such as, e.g. alcohols, aloe vera gel, allantoin, glycerine, vitamin A and E oils, mineral oil,PPG2 myristyl propionate, and the like to form, e.g. alcoholic solutions, topical cleansers, cleansing creams, skin gels, skin lotions, and shampoos in cream or gel formulations.

The vaccine or immunogens of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Vaccine or immunogens of the present invention may also be delivered by the use of monoclonal antibodies as individual carriers to which the vaccine or immunogen molecules are coupled. The vaccine or immunogens of the present invention may also be coupled with soluble polymers as targetable vaccine or immunogen carriers. Such polymers can include polyvinyl-pyrrolidone, pyran copolymer, polyhydroxypropylmethacryl-amidephenol, polyhydroxyethylaspartamidephenol, or polyethyleneoxidemolylysine substituted with palmitoyl residues. Furthermore, the vaccine or immunogens of the present invention may be coupled to a class of biodegradable polymers useful in achieving controlled release of a vaccine or immunogen, for example, polyactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Up to this point a general description has been given of the subjects of the present invention. With the assistance of the following examples, a more detailed description will now be given of specific embodiments of the invention, aimed at giving a better understanding of the objects, characteristics, advantages and methods of application thereof. The following examples refer, respectively, to embodiments of the process for the preparation of immunogens and diagnostic reagents against a specific pathogenic agent, according to the present invention; to a demonstration of the effectiveness of the clones selected for preparation of immunogens based on the effects produced by samples of serum from test animals immunized using the single clones; and to a demonstration of the effectiveness of the clones selected for preparation of diagnostic reagents, based on their specific reaction with the serum of individuals immunized with HBsAg.

The single FIGURE enclosed shows a portion of the genetic map of the plasmid pC89 engineered for the purposes of the invention. The nucleotidic sequence for the restriction sites and the corresponding aminoacidic sequence are illustrated below the portion of the above mentioned genetic map. The wild-type aminoacidic sequence of the amino-terminal end of mature pVIII has been modified in order to introduce single EcoRI and BamHI sites.

EXAMPLE 1

Process for the Preparation of Specific Diagnostic Reagents and Immunogens for the Disease Caused by the Human Hepatitis B Virus (HBV)

The following process was used according to the invention:

A first "library" of epitopes was prepared, made up of phages having oligopeptides with 9 amino acids displayed on the surface of the capsid, expressed by random sequence oligonucleotidic inserts introduced into the gene coding for the protein VIII of the phage capsid. For expression of the recombinant proteins containing the epitope, the plasmid pC89 was used, engineered as described in F. Felici et al., Selection of Antibody Ligands from a Large Library of oligopeptides Expressed on a Multivalent Exposition Vector, J. Mol. Biol. (1991), 222, 301–310, of which a portion of the genetic map is shown in the FIGURE.

A second epitope "library" was prepared in the same way as the first, with the difference that two cysteine residues are present at the two ends of the insert, as described in A. Luzzago et al., Mimicking of discontinuous epitopes by phage displayed peptides, I. Epitope mapping of human H Ferritin using a phage library of contrained peptides, Gene (1993), 128, 51–57.

A sample of sera from individuals immunized using a recombinant form of the HBV surface antigen (HBsAg) was tested for the presence of specific antibodies against HBsAg. The sera with a high antibody content against HBsAg were then used.

The antibodies contained in these sera were immobilized on a solid matrix and incubated with the phage libraries. The phages specifically retained by these antibodies were then eluted and amplified.

Bacteria infected by the phages selected as above were plated on a solid culture medium and transferred onto nitrocellulose filters. Subsequently, these filters were incubated with sera from individuals immunized against HBsAg different from the serum used for the first enrichment. The phages specifically recognized by antibodies present in these sera were identified and isolated.

The phages identified as above were counter-selected for reactivity to antibodies present in the sera of individuals not immune to HBsAg, using the ELISA test.

The phages resulting from this counter-selection were checked for specificity of reaction to anti-HBsAg antibodies by means of competition in the ELISA test.

The nucleotidic sequence coding for the epitopes identified in this manner was subsequently determined (SEQ ID NO: 4, 5, 6, 8).

EXAMPLE 2

Demonstration of the Effectiveness of the Selected Phases as Specific Immunogens for the Disease Caused by the Human Hepatitis Virus (HBV)

The following process was used:

The phages, selected as described above, were amplified and purified.

The purified phages were injected into test animals (mice, rats and rabbits), according to the process described by V. F. de la Cruz et al., Immunogenicity and Epitope Mapping of Foreign Sequences via Genetically Engineered Filamentous Phage, J. Biol. Chem. (1988) 263, 9, 4318–4322, and by J. Greenwood et al., Multiple Display of Foreign Peptides on a Filamentous Bacteriophage, J. Mol. Biol. (1991) 220, 821–827.

The sera of animals immunized as above were tested for the presence of antibodies capable of interacting with HBsAg, using the ELISA test. This method underlined the presence of a high level of anti-HBsAg antibodies in the serum of test animals immunized as above.

The same immunization process was adopted, using as immunogens synthetic oligopeptides reproducing the amino acid sequence (SEQ ID from NO: 1 to NO: 3 and NO:7) of the epitopes identified according to the procedure given above. This method underlined the presence of a high level of anti-HBsAg antibodies in the serum of test animals immunized as above.

The same immunization process was adopted, using as immunogens recombinant forms produced in bacteria of the heavy chain of human ferritin displaying on their surface the synthetic oligopeptides reproducing the amino acid sequence of the epitopes identified according to the procedure given above. This method underlined the presence of a high level of anti-HBsAg antibodies in the serum of test animals immunized as above.

EXAMPLE 3

Demonstration of the Effectiveness of the Selected Phases as Diagnostic Reagents for Determination of the Presence of Anti-HBsAg Antibodies in Serum A process comprising the following operations was used:

20 human sera from individuals vaccinated against HBsAg were analyzed in an ELISA test for their ability to recognize specifically the phage clones, identified as described in example 1, showing the peptide sequences described (SEQ ID from NO: 1 to NO: 3 and NO: 7). The results show that 80% of the sera specifically recognize at least one of the four sequences selected.

16 human serums from patients suffering from hepatitis B and containing anti-HBsAg antibodies were analyzed in an ELISA test for their ability to recognize specifically the phage clones, identified as described in example 1, showing the peptide sequences described (SEQ ID from NO: 1 to NO: 3 and NO:7). The results show that 44% of the sera specifically recognize at least one of the four sequences selected.

20 human sera from individuals not vaccinated against HBsAg were analyzed in an ELISA test for their ability to recognize specifically the phage clones, identified as described in example 1, displaying the peptide sequences described (SEQ ID from NO: 1 to NO:3 and NO:7). The results show that none of the sera specifically recognize any of the four sequences selected.

EXAMPLE 4

Process for the Preparation of Specific Diagnostic Reagents and Immunogens for the Disease Caused by the Human Hepatitis C Virus (HCV)

The following process was used according to the invention:

A first "library" of epitopes was prepared, made up of phages having oligopeptides with 9 amino acids displayed on the surface of the capsid, expressed by random sequence oligonucleotidic inserts introduced into the gene coding for the protein VIII of the phage capsid. For the expression of the recombinant proteins containing the epitope, the plasmid pCS89 was used, engineered as described in F. Felici et al., Selection of Antibody Ligands from a Large Library of oligopeptides Expressed on a Multivalent Exposition Vector, J. Mol. Biol. (1991), 222, 301–310, of which a portion of the genetic map is shown in the FIGURE.

A second epitope "library" was prepared in the same way as the first, with the difference that two cysteine residues are present at the two ends of the insert, as described in A.

Luzzago et al., Mimicking of discontinuous epitopes by phage displayed peptides, I. Epitope mapping of human H Ferritin using a phage library of contrained peptides, Gene (1993), 128, 51–57.

Sera from patients clinically characterized by being infected with the hepatitis C virus were then used.

The antibodies contained in these sera were immobilized on a solid matrix and incubated with the phage libraries. The phages specifically retained by these antibodies were then eluted and amplified.

Bacteria infected by the phages selected as above were plated on a solid culture medium and transferred onto nitrocellulose filters. Subsequently, these filters were incubated with serums from patients infected with HCV, different from the serum used for the initial enrichment. The phages specifically recognized by antibodies present in these sera were identified and isolated.

The phages identified as above were counter-selected for reactivity to antibodies present in the sera of individuals not infected with HCV, using the ELISA test.

The reaction specificity of the above phages with anti-HCV antibodies is evaluated statistically as follows. The frequency with which a significant number of sera from patients infected with HCV recognize the phage clones is determined in an ELISA test. In parallel, again using the ELISA test, absence of recognition of the same phage clones by a significant number of sera from individuals not infected with HCV is tested. For each phage clone, the specificity is evaluated by comparison of the frequence of recognition by sera from patients infected with HCV with that of sera from non-infected individuals.

The epitope peptidic sequence identified in this manner was subsequently determined (SEQ ID from NO: 9 to NO: 30).

EXAMPLE 5

Demonstration of the Effectiveness of the Selected Phages as Diagnostic Reagents for Determination of the Presence of Anti-HCV Antibodies in Serum A process comprising the following operations was used:

40 human sera from individuals not infected with HCV were analyzed in an ELISA test for their ability to recognize specifically the phage clones, identified as described in example 4, displaying the peptide sequences described (SEQ ID from NO: 9 to NO: 23). The results show that none of the sera recognizes the sequences selected.

42 human sera from patients infected with HCV were analyzed in an ELISA test for their ability to recognize specifically the phage clones, identified as described in example 4, displaying the peptide sequences described (SEQ ID from NO: 9 to NO: 23). The results show that each phage clone is recognized specifically by the sera selected, with a frequency varying from 15 to 65% (see table I). The same results also show that each of the 42 sera tested specifically recognizes at least one of the sequences selected.

The sequences selected give an effective indication of the presence of anti-HCV antibodies in the blood of all patients examined, and do not react with blood from non-infected individuals. These data show that the group of phage clones selected forms a reliable system for the diagnosis of infection by the hepatitis C virus.

TABLE 1

| Seq. Id | c1 | c2 | c3 | c4 | c5 | c6 | c7 | c8 | c9 | c10 | c11 | c12 | c13 | c14 | c15 | c16 | c17 | c18 | c19 | c20 | c21 | Sequence |
|---|---|---|---|---|---|---|---|---|---|---|---|---|---|---|---|---|---|---|---|---|---|---|
| 9 | | | | | | | | | | | | | | | | | | | | | | LPAHGPSLS |
| 10 | | | | | | | | | | | | | | | | | | | | | | LPWGVAARR |
| 11 | | | | | | | | | | | | | | | | | | | | | | PTHYTTSAP |
| 12 | | | | | | | | | | | | | | | | | | | | | | PTHYISSRH |
| 13 | | | | | | | | | | | | | | | | | | | | | | PTHYISTSL |
| 14 | | | | | | | | | | | | | | | | | | | | | | TRHYLRPGL |
| 15 | | | | | | | | | | | | | | | | | | | | | | PSHYVPRIY |
| 16 | | | | | | | | | | | | | | | | | | | | | | PPHLTLSSCR |
| 17 | | | | | | | | | | | | | | | | | | | | | | KLNSRGSIS |
| 18 | | | | | | | | | | | | | | | | | | | | | | GKFPGSKPS |
| 19 | | | | | | | | | | | | | | | | | | | | | | FPGGPPLRA |
| 20 | | | | | | | | | | | | | | | | | | | | | | APSLPAGYL |
| 21 | | | | | | | | | | | | | | | | | | | | | | VPQSRLEPW |
| 22 | | | | | | | | | | | | | | | | | | | | | | NKREWAPPP |
| 23 | | | | | | | | | | | | | | | | | | | | | | NKTKQNPNL |

TABLE 1-continued

| Seq. Id | c22 | c23 | c24 | c25 | c26 | c27 | c28 | c29 | c30 | c31 | c32 | c33 | c34 | c35 | c36 | c37 | c38 | c39 | c40 | c41 | c42 | Sequence |
|---|---|---|---|---|---|---|---|---|---|---|---|---|---|---|---|---|---|---|---|---|---|---|
| 9 | P | P | P | P | P | P | P | P | P | P | P | P |  | P |  | P |  |  |  | P |  | LPAHGPSLS |
| 10 |  | P | P | P |  | P |  |  |  | P | P | P |  |  | P |  |  |  |  | P |  | LPWGVAARR |
| 11 |  |  |  | P |  | P |  | P |  |  |  |  |  |  |  |  |  |  |  | P |  | PTHYTTSAP |
| 12 | P |  | P |  | P |  | P |  | P |  | P | P |  | P |  | P |  | P |  | P |  | PTHYISSRH |
| 13 | P | P | P |  |  |  | P |  | P |  | P |  |  |  | P |  | P |  |  | P |  | PTHYISTSL |
| 14 | P |  | P |  | P |  | P |  |  |  |  |  |  |  |  |  |  |  |  | P |  | TRHYLRPGL |
| 15 | P |  |  | P | P |  |  |  |  |  | P |  |  |  |  |  |  |  |  | P |  | PSHYVPRIY |
| 16 | P |  |  |  | P |  |  |  |  |  |  |  |  |  | P |  | P |  |  | P |  | PPHLTLSSCR |
| 17 |  |  |  |  |  |  |  |  |  |  | P | P |  | P |  | P | P | P | P | P |  | KLNSRGSIS |
| 18 |  | P |  |  | P |  |  | P |  | P | P |  |  |  |  |  |  |  |  |  |  | GKFPGSKPS |
| 19 |  |  | P |  |  | P |  |  |  | P | P |  |  |  |  |  |  |  |  |  |  | FPGGPPLRA |
| 20 | P | P |  | P |  |  |  |  |  | P | P |  |  |  |  |  | P |  |  | P |  | APSLPAGYL |
| 21 | P |  |  | P |  |  |  |  |  |  |  |  | P |  |  |  |  |  |  | P |  | VPQSRLEPW |
| 22 | P |  | P |  |  | P |  |  |  |  |  |  |  |  |  |  |  |  |  |  |  | NKREWAPPP |
| 23 |  |  |  |  |  |  |  |  |  |  |  |  |  |  |  |  |  |  |  |  |  | NKTKQNPNL |

■ "= Positive"   ▨ "= Negative"   ☐ "= Not analized"

EXAMPLE 6
Process for the Preparation of Specific Diagnostic Reagents and Immunogens for the Disease Type II Cryoglobulinemia Caused by and/or Associated with the Human Hepatitis C Virus (HCV)

The following process was used according to the invention:

A first "library" of epitopes was prepared, made up of phages displaying oligopeptides with 9 amino acids on the surface of the capsid, expressed by random sequence oligonucleotidic inserts introduced into the gene coding for the protein VIII of the phage capsid. For expression of the recombinant proteins containing the epitope, the plasmid pC89 was used, engineered as described in F. Felici et al., Selection of Antibody Ligands from a Large Library of Oligopeptides Expressed on a Multivalent Exposition Vector, J. Mol. Biol. (1991), 222, 301–310, of which a portion of the genetic map is shown in the FIGURE.

A second epitope "library" was prepared in the same way as the first, with the difference that two cysteine residues are present at the two ends of the insert, as described in A. Luzzago et al., Mimicking of discontinuous epitopes by phage displayed peptides, I. Epitope mapping of human H Ferritin using a phage library of contrained peptides, Gene (1993), 128, 51–57.

Samples of antibodies from individuals suffering from type II Cryoglobulinemia caused by and/or associated with the human hepatitis C virus (HCV) were immobilized on a solid matrix and incubated with the phage libraries. The phages specifically retained by said antibody were then eluted and amplified.

Bacteria infected by the phages selected as above were plated on a solid culture medium and transferred onto nitrocellulose filters. Subsequently, these filters were incubated with sera from patients suffering from type II Cryoglobulinemia caused by and/or associated with human hepatitis C virus (HCV), different from the serum used for the first enrichment. The phages specifically recognized by antibodies present in these serums were identified and isolated.

The phages identified as above were counter-selected for reactivity to antibodies present in the serums of individuals not infected with type II Cryoglobulinemia caused by and/or associated with human hepatitis C virus (HCV), using the ELISA test.

The reaction specificity of the phages resulting from this counter-selection with antibodies specific for Type II Cryoglobulinemia caused by and/or associated with the human hepatitis C virus is evaluated statistically as follows. The frequency with which a significant number of sera from patients suffering from type II Cryoglobulinemia caused by and/or associated with the human hepatitis C virus (HCV) recognize the phage clones is determined in an ELISA test. In parallel, again using the ELISA test, absence of recognition of the same phage clones by a significant number of sera from individuals not suffering from the disease is tested. For each phage clone, the specificity is evaluated by comparison of the frequency of recognition by sera from patients suffering from the disease with that of sera from healthy individuals.

The epitope peptidic sequence identified in this manner was subsequently determined (SEQ ID from NO: 31 to NO: 42).

EXAMPLE 7
Demonstration of the Effectiveness of the Selected Phages as Diagnostic Reagents for Determination of the Presence in the Serum of Antibodies Specific for the Disease Type II Cryoglobulinemia Caused by and/or Associated with the Human Hepatitis C Virus (HCV)

A process comprising the following operations was used:

16 human sera from individuals not suffering from type II Cryoglobulinemia, caused by and/or associated with the human hepatitis C virus (HCV), were analyzed in an ELISA test for their ability to recognize specifically the phage clones, identified as described in example 6, showing the peptide sequences described (SEQ ID from NO: 31 to NO: 42). The results show that none of the serums recognizes the sequences selected.

80 human sera from patients suffering from type II Cryoglobulinemia, caused by and/or associated with the human hepatitis C virus (HCV), were analyzed in an ELISA test for their ability to recognize specifically the phage clones, identified as described in example 6, displaying the peptide sequences described (SEQ ID from NO: 31 to NO: 42). The results show that each phage clone is recognized specifically by the sera selected, with a frequency varying from 15 to 60%.

The sequences selected give an effective indication of the presence of antibodies specific for type II Cryoglobulinemia, caused by and/or associated with the human hepatitis C virus (HCV), in the blood of all patients examined, and do not react with blood from individuals not suffering from the disease. These data show that the group of phage clones selected forms a reliable system for diagnosis of the disease type II Cryoglobulinemia caused by and/or associated with the human hepatitis C virus (HCV).

The sequences selected show significant homology with the human LAG-3 gene sequence, which is specifically expressed by T lymphocytes and "natural killer" cells. The same antibodies used to select the phage clones react with the portion of the protein LAG-3 that is homologous with the sequence of the selected phage clones. This recognition can be abolished by competition with the selected phage clones. These results indicate that the selected phage clones can be used to block the autoantibody binding to the protein LAG-3.

EXAMPLE 8

Process for the Preparation of Diagnostic Reagents for Type I Diabetes Autoimmune Disease and Demonstration of the Effectiveness of the Selected Phages as Diagnostic Reagents for Determination of the Presence in the Blood of Autoantibodies Characterization Autoimmune Diseases The following process was used according to the invention:

A first "library" of epitopes was prepared, made up of phages having oligopeptides with 9 amino acids displayed on the surface of the capsid, expressed by random sequence oligonucleotidic inserts introduced into the gene coding for the protein VIII of the phage capsid. For expression of the recombinant proteins containing the epitope, the plasmid pC89 was used, engineered as described in F. Felici et al., Selection of Antibody Ligands from a Large Library of Oligopeptides Expressed on a Multivalent Exposition Vector, J. Mol. Biol. (1991), 222, 301–310.

A second epitope "library" was prepared in the same way as the first, with the difference that two cysteine residues are present at the two ends of the insert, as described in A. Luzzago et al., Mimicking of discontinuous epitopes by phage displayed peptides, I. Epitope mapping of human H. Ferritin using a phage library of constrained peptides, Gene (1993), 128, 51–57.

A sample of sera from diabetic patients at the beginning of their type I diabetes clinical history was tested for the presence of antibodies specific for certain known markers characteristic of the disease, such as anti-insulin and ICA antibodies, or antibodies against the pancreatic islets. A serum with a high antibody content was then used for selection.

The antibodies contained in this serum were immobilized on a solid matrix and incubated with the phage libraries. The phages specifically retained by these antibodies were then eluted and amplified.

Bacteria infected by the phages selected as above were plated on a solid culture medium and transferred onto nitrocellulose filters. Subsequently, these filters were incubated with sera from diabetic individuals different from the serum used for the first enrichment. The phages specifically recognized by antibodies present in these sera were identified and isolated.

The phages identified as above were counter-selected for reactivity to antibodies present in the sera of individuals not suffering from type I diabetes, using the ELISA test.

The phages resulting from this counter-selection were checked for specificity of reaction by means of large scale screening using sera from diabetic patients at different stages of the disease. The nucleotidic sequence coding for the epitopes identified in this manner was then determined.

The phage clones were analyzed using the following process:

25 human sera taken from individuals at the time of the first clinical appearance of type I diabetes were analyzed using an ELISA test for their ability to recognize specifically the phage clones, identified as described and displaying the peptide sequences described (SEQ ID NO: 43, SEQ ID NO: 44, SEQ ID NO: 45, SEQ ID NO: 46, SEQ ID NO: 47). The results show that 36% of the sera recognized specifically at least one of the 5 sequences selected.

16 human sera taken from individuals with autoimmune pathologies other than diabetes were analyzed using an ELISA test for their ability to recognize specifically the phage clones, identified as described in example 8, and displaying the peptide sequences described (SEQ ID NO: 43, SEQ ID NO: 44, SEQ ID NO: 45, SEQ ID NO: 46, SEQ ID NO: 47). The results show that 18% of the sera recognized specifically at least one of the 5 sequences selected.

50 human sera taken from individuals not suffering from diabetes or from other autoimmune pathologies were analyzed using an ELISA test for their ability to recognize specifically the phage clones, identified as described in example 8, and displaying the peptide sequences described (SEQ ID NO: 43, SEQ ID NO: 44, SEQ ID NO: 45, SEQ ID NO: 46; SEQ ID NO: 47). The results show that none of the sera recognized specifically any of the 5 sequences selected.

EXAMPLE 9

Process for the Preparation of Diagnostic Reagents and Immunogens Specific for Detection and Induction of the Immune Response of the Human Tumoral Protein NEU (p185$^{HER2}$)

The following process was used according to the invention:

The monoclonal antibodies MGr2 and MGr6 were identified as recognizing specifically the human tumoral protein NEU (p185$^{HER2}$).

Two epitope "libraries" were prepared, made up of phages displaying oligopeptides on the surface of the capsid (as described in example 1), which were then examined using the biopanning method (V. Parmley, S. F. & Smith, G. P., Antibody-selectable filamentous fd phage vectors: affinity purification of target genes, Gene (1988) 73, 305–318) to select the clones that react specifically with the above mentioned antibodies.

Bacteria infected by the phages selected as above were plated on a solid culture medium and transferred onto nitrocellulose filters. Subsequently, these filters were incubated with the monoclonal antibodies MGr2 and MGr6. The reaction specificity of the phages identified in this way was controlled using the ELISA test.

The peptidic sequence of the epitopes identified as above was subsequently determined by means of analysis of the corresponding nucleotidic coding sequence (for MGr2 SEQ ID from NO: 48 to NO: 56, for MGr6 SEQ ID from NO: 57 to NO: 68).

The phages, selected as above, were amplified, purified and injected into test animals according to the procedure described in Example 2. The serum from animals immunized in this manner was tested for the presence of antibodies capable of interacting with NEU, using the immunohistochemical test.

This method underlined the presence of a significant level of anti-NEU antibodies in the blood of test animals immunized in this manner.

The results obtained with the phages described in this example demonstrate the effectiveness of said phages as antigenic and immunogenic substitutes of the human tumoral protein NEU. This may allow the phages thus obtained, or derivatives thereof, to be used as reagents for the detection of anti-NEU antibodies in sera from patients suffering from tumors and/or as specific immunogens to stimulate an anti-NEU antibody response.

We claim:

1. A process for preparation of a peptide that mimics an antigen or a pathogenic organism specific to a disease, comprising the steps of:

(a) collecting serum samples from at least two patients whose sera contain antibodies to the antigen or pathogenic organism and from at least one control individual whose serum would not be expected to contain antibodies to the antigen or pathogenic organism;

(b) contacting the antibodies from the serum sample from said first patient with a phage-displayed random peptide library and selecting a first pool of phages which are bound by antibodies present in the serum sample from said first patient;

(c) contacting the phages in said first pool of phages with the antibodies from a serum sample from said second patient and selecting a second group of phages that are bound by antibodies present in samples from both said first patient and from said second patient;

(d) contacting phages from the second group with serum from said control individual to identify phages that are not bound by antibodies contained in the sera from said control individual; and (e) if a phage is bound by antibodies in the sera from at least both said first and second patients but is not bound by antibodies contained in the serum from said control individual, identifying and producing the peptide displayed by said phage.

2. A process in accordance with claim 1 further including, prior to said step (d), contacting phages from the second group produced in step (c) with a serum sample from a third patient whose serum contains antibodies to the antigen or pathogenic organism and selecting a third group of phages that are bound by antibodies present in samples from all of said first, second and third patients, wherein the phages from the second group as used in step (d) comprise phages from the third group.

3. A process in accordance with claim 1, wherein said phage-displayed random peptide library is one prepared using filamentous phages selected from the group consisting of M13, F1, Fd and derivatives thereof.

4. A process in accordance with claim 1, wherein said phage-displayed random peptide library is one in which the random sequence oligonucleotidic inserts are inserted into the gene coding for protein VIII of the phage capsid.

5. A process in accordance with claim 3, wherein said phage-displayed random peptide library is one in which the random sequence oligonucleotidic inserts are inserted into the gene coding for protein III of the phage capsid.

6. A process in accordance with claim 1, wherein said antigen or pathogenic organism is one selected from the group consisting of the surface antigen of the virus of human hepatitis B (HBsAg), the virus of human hepatitis C, and antigens pathogenically linked to an autoimmune disease.

7. A process in accordance with claim 6, wherein the patient is one who has been immunized with HBsAg or one infected with the virus of human hepatitis C.

8. A process in accordance with claim 1, wherein said phage-displayed random peptide library is one in which the random sequence oligonucleotide inserts are inserted using the plasmid pc89 as a vector.

* * * * *

```
                          SEQUENCE LISTING (1) GENERAL INFORMATION:

(iii) NUMBER OF SEQUENCES: 68

(2) INFORMATION FOR SEQ ID NO: 1:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: recombinant protein (iii) HYPOTHETICAL: yes (v) FRAGMENT TYPE: internal (vii) IMMEDIATE SOURCE:
         (A) LIBRARY: of recombinant peptides on phage
         (B) CLONE: phagic (ix) FEATURE:
         (A) NAME/KEY: polypeptide
         (B) IDENTIFICATION METHOD: selection with specific antibodies (xi) SEQUENCE DESCRIPTION: SEQ ID NO: 1:

Glu Phe Cys Arg Thr Cys Ala His Pro Gly Glu His Ala Gly Asp
1               5                  10                  15

(2) INFORMATION FOR SEQ ID NO: 2:

(i) SEQUENCE CHARACTERISTICS:
         (A) LENGTH: 15 amino acid
         (B) TYPE: amino acid
         (C) STRANDEDNESS: single
         (D) TOPOLOGY: linear (ii) MOLECULE TYPE: recombinant protein (iii) HYPOTHETICAL: yes (v) FRAGMENT TYPE: internal (vii) IMMEDIATE SOURCE:
         (A) LIBRARY: of recombinant peptides on phage
         (B) CLONE: phagic (ix) FEATURE:
         (A) NAME/KEY: polypeptide
         (B) IDENTIFICATION METHOD: selection with specific antibodies (xi) SEQUENCE DESCRIPTION: SEQ ID NO: 2:

Glu Phe Cys Gly Pro Phe Tyr Leu Ser Ala Pro Gln Cys Gly Asp
1               5                  10                  15

(2) INFORMATION FOR SEQ ID NO: 3:

(i) SEQUENCE CHARACTERISTICS:
         (A) LENGTH: 15 amino acids
```

```
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 3:

Glu Phe Cys Gly Pro Phe Phe Leu Ala Ala Ser Val Cys Gly Asp
1               5                   10                  15

(2) INFORMATION FOR SEQ ID NO: 4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (iii) HYPOTHETICAL: no (iv) ANTI-SENSE: no (v) FRAGMENT TYPE: internal (vii) IMMEDIATE SOURCE:
        (A) LIBRARY: of recombinant peptides on phage (ix) FEATURE:
        (A) NAME/KEY: polynucleotide
        (B) IDENTIFICATION METHOD: selection with specific antibodies (xi) SEQUENCE DESCRIPTION: SEQ ID NO: 4:

GAATTCTGCC GAACCTGCGC CCATCCAGGT GAGCATGCGG GGGATCC                47

(2) INFORMATION FOR SEQ ID NO: 5:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (iii) HYPOTHETICAL: no (iv) ANTI-SENSE: no (v) FRAGMENT TYPE: internal (vii) IMMEDIATE SOURCE:
        (A) LIBRARY: of recombinant peptides on phage (ix) FEATURE:
        (A) NAME/KEY: polynucleotide
        (B) IDENTIFICATION METHOD: selection with specific antibodies (xi) SEQUENCE DESCRIPTION: SEQ ID NO: 5:

GAATTCTGCG GGCCTTTTTA TCTCTCTGCA CCTCAGTGCG GGGATCC                 47
```

(2) INFORMATION FOR SEQ ID NO: 6:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (iii) HYPOTHETICAL: no (iv) ANTI-SENSE: no (v) FRAGMENT TYPE: internal (vii) IMMEDIATE SOURCE:
        (A) LIBRARY: of recombinant peptides on phage (ix) FEATURE:
        (A) NAME/KEY: polynucleotide
        (B) IDENTIFICATION METHOD: selection with specific antibodies (xi) SEQUENCE DESCRIPTION: SEQ ID NO: 6:

```
GAATTCTGCG GTCCCTTCTT TCTCGCGGCT TCCGTATGCG GGGATCC                    47
```

(2) INFORMATION FOR SEQ ID NO: 7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 7:

```
Glu Phe Cys Gly Pro Phe Phe Leu Ser Pro Thr Ser Cys Gly Asp
1               5                   10                  15
```

(2) INFORMATION FOR SEQ ID NO: 8:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (iii) HYPOTHETICAL: no (iv) ANTI-SENSE: no (v) FRAGMENT TYPE: internal (vii) IMMEDIATE SOURCE:
        (A) LIBRARY: of recombinant peptides on phage (ix) FEATURE:
        (A) NAME/KEY: polynucleotide
        (B) IDENTIFICATION METHOD: selection with specific antibodies (xi) SEQUENCE DESCRIPTION: SEQ ID NO: 8:

```
GAATTCTGCG GTCCGTTTTT TCTCTCCCCG ACGTCATGCG GGGATCC   47
```

(2) INFORMATION FOR SEQ ID NO: 9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 9:

```
Glu Phe Cys Leu Pro Ala His Gly Pro Ser Leu Ser Cys Gly Asp
1               5                  10                  15
```

(2) INFORMATION FOR SEQ ID NO: 10:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 10:

```
Glu Phe Cys Leu Pro Trp Gly Val Ala Ala Arg Arg Cys Gly Asp
1               5                  10                  15
```

(2) INFORMATION FOR SEQ ID NO: 11:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide

```
        (B) IDENTIFICATION METHOD: selection with specific antibodies (xi) SEQUENCE DESCRIPTION: SEQ ID NO: 11:

Glu Phe Cys Pro Thr His Tyr Thr Thr Ser Ala Pro Cys Gly Asp
1               5                   10                  15

(2) INFORMATION FOR SEQ ID NO: 12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 12:

Glu Phe Cys Pro Thr His Tyr Ile Ser Ser Arg His Cys Gly Asp
1               5                   10                  15

(2) INFORMATION FOR SEQ ID NO: 13:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 13:

Glu Phe Cys Pro Thr His Tyr Ile Ser Thr Ser Leu Cys Gly Asp
1               5                   10                  15

(2) INFORMATION FOR SEQ ID NO: 14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
```

(B) CLONE: phagic (ix) FEATURE:
                (A) NAME/KEY: polypeptide
                (B) IDENTIFICATION METHOD: selection with specific antibodies (xi) SEQUENCE DESCRIPTION: SEQ ID NO: 14:

Glu Phe Cys Thr Arg His Tyr Leu Arg Pro Gly Leu Cys Gly Asp
1               5                   10                  15

(2) INFORMATION FOR SEQ ID NO: 15:

(i) SEQUENCE CHARACTERISTICS:
                (A) LENGTH: 15 amino acids
                (B) TYPE: amino acid
                (C) STRANDEDNESS: single
                (D) TOPOLOGY: linear (ii) MOLECULE TYPE: recombinant protein (iii) HYPOTHETICAL: yes (v) FRAGMENT TYPE: internal (vii) IMMEDIATE SOURCE:
                (A) LIBRARY: of recombinant peptides on phage
                (B) CLONE: phagic (ix) FEATURE:
                (A) NAME/KEY: polypeptide
                (B) IDENTIFICATION METHOD: selection with specific antibodies (xi) SEQUENCE DESCRIPTION: SEQ ID NO: 15:

Glu Phe Cys Pro Ser His Tyr Val Pro Arg Ile Tyr Cys Gly Asp
1               5                   10                  15

(2) INFORMATION FOR SEQ ID NO: 16:

(i) SEQUENCE CHARACTERISTICS:
                (A) LENGTH: 15 amino acids
                (B) TYPE: amino acid
                (C) STRANDEDNESS: single
                (D) TOPOLOGY: linear (ii) MOLECULE TYPE: recombinant protein (iii) HYPOTHETICAL: yes (v) FRAGMENT TYPE: internal (vii) IMMEDIATE SOURCE:
                (A) LIBRARY: of recombinant peptides on phage
                (B) CLONE: phagic (ix) FEATURE:
                (A) NAME/KEY: polypeptide
                (B) IDENTIFICATION METHOD: selection with specific antibodies (xi) SEQUENCE DESCRIPTION: SEQ ID NO: 16:

Glu Phe Cys Pro Pro His Leu Thr Leu Ser Ser Cys Arg Gly Asp
1               5                   10                  15

(2) INFORMATION FOR SEQ ID NO: 17:

(i) SEQUENCE CHARACTERISTICS:
                (A) LENGTH: 15 amino acids
                (B) TYPE: amino acid
                (C) STRANDEDNESS: single
                (D) TOPOLOGY: linear (ii) MOLECULE TYPE: recombinant protein (iii) HYPOTHETICAL: yes (v) FRAGMENT TYPE: internal (vii) IMMEDIATE SOURCE:
            (A) LIBRARY: of recombinant peptides on phage
            (B) CLONE: phagic (ix) FEATURE:
            (A) NAME/KEY: polypeptide
            (B) IDENTIFICATION METHOD: selection with specific antibodies (xi) SEQUENCE DESCRIPTION: SEQ ID NO: 17:

Glu Phe Cys Lys Leu Asn Ser Arg Gly Ser Ile Ser Cys Gly Asp
1               5                   10                  15

(2) INFORMATION FOR SEQ ID NO: 18:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: recombinant protein (iii) HYPOTHETICAL: yes (v) FRAGMENT TYPE: internal (vii) IMMEDIATE SOURCE:
            (A) LIBRARY: of recombinant peptides on phage
            (B) CLONE: phagic (ix) FEATURE:
            (A) NAME/KEY: polypeptide
            (B) IDENTIFICATION METHOD: selection with specific antibodies (xi) SEQUENCE DESCRIPTION: SEQ ID NO: 18:

Glu Phe Cys Gly Lys Phe Pro Gly Ser Lys Pro Ser Cys Gly Asp
1               5                   10                  15

(2) INFORMATION FOR SEQ ID NO: 19:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: recombinant protein (iii) HYPOTHETICAL: yes (v) FRAGMENT TYPE: internal (vii) IMMEDIATE SOURCE:
            (A) LIBRARY: of recombinant peptides on phage
            (B) CLONE: phagic (ix) FEATURE:
            (A) NAME/KEY: polypeptide
            (B) IDENTIFICATION METHOD: selection with specific antibodies (xi) SEQUENCE DESCRIPTION: SEQ ID NO: 19:

Glu Phe Cys Phe Pro Gly Gly Pro Pro Leu Arg Ala Cys Gly Asp
1               5                   10                  15

(2) INFORMATION FOR SEQ ID NO: 20:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: recombinant protein (iii) HYPOTHETICAL: yes (v) FRAGMENT TYPE: internal (vii) IMMEDIATE SOURCE:
            (A) LIBRARY: of recombinant peptides on phage
            (B) CLONE: phagic (ix) FEATURE:
            (A) NAME/KEY: polypeptide
            (B) IDENTIFICATION METHOD: selection with specific antibodies (xi) SEQUENCE DESCRIPTION: SEQ ID NO: 20:

Glu Phe Cys Ala Pro Ser Leu Pro Ala Gly Tyr Leu Cys Gly Asp
1               5                   10                  15

(2) INFORMATION FOR SEQ ID NO: 21:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: recombinant protein (iii) HYPOTHETICAL: yes (v) FRAGMENT TYPE: internal (vii) IMMEDIATE SOURCE:
            (A) LIBRARY: of recombinant peptides on phage
            (B) CLONE: phagic (ix) FEATURE:
            (A) NAME/KEY: polypeptide
            (B) IDENTIFICATION METHOD: selection with specific antibodies (xi) SEQUENCE DESCRIPTION: SEQ ID NO: 21:

Glu Phe Cys Gln Val Pro Gln Ser Arg Leu Glu Pro Trp Gly Asp
1               5                   10                  15

(2) INFORMATION FOR SEQ ID NO: 22:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: recombinant protein (iii) HYPOTHETICAL: yes (v) FRAGMENT TYPE: internal (vii) IMMEDIATE SOURCE:
            (A) LIBRARY: of recombinant peptides on phage
            (B) CLONE: phagic (ix) FEATURE:
            (A) NAME/KEY: polypeptide
            (B) IDENTIFICATION METHOD: selection with specific antibodies (xi) SEQUENCE DESCRIPTION: SEQ ID NO: 22:

Glu Phe Asn Lys Arg Glu Trp Ala Pro Pro Pro Asp
1               5                   10      12

(2) INFORMATION FOR SEQ ID NO: 23:

(i) SEQUENCE CHARACTERISTICS:
            (A) LENGTH: 12 amino acids (B) TYPE: amino acid
          (C) STRANDEDNESS: single
          (D) TOPOLOGY: linear (ii) MOLECULE TYPE: recombinant protein (iii) HYPOTHETICAL: yes (v) FRAGMENT TYPE: internal (vii) IMMEDIATE SOURCE:
          (A) LIBRARY: of recombinant peptides on phage
          (B) CLONE: phagic (ix) FEATURE:
          (A) NAME/KEY: polypeptide
          (B) IDENTIFICATION METHOD: selection with specific antibodies (xi) SEQUENCE DESCRIPTION: SEQ ID NO: 23:

Glu Phe Asn Lys Thr Lys Gln Asn Pro Asn Leu Asp
1               5                  10          12

(2) INFORMATION FOR SEQ ID NO: 24:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: recombinant protein (iii) HYPOTHETICAL: yes (v) FRAGMENT TYPE: internal (vii) IMMEDIATE SOURCE:
          (A) LIBRARY: of recombinant peptides on phage
          (B) CLONE: phagic (ix) FEATURE:
          (A) NAME/KEY: polypeptide
          (B) IDENTIFICATION METHOD: selection with specific antibodies (xi) SEQUENCE DESCRIPTION: SEQ ID NO: 24:

Glu Phe Thr Ser Leu Gln Pro Asp Arg Ala Gln Asp
1               5                  10          12

(2) INFORMATION FOR SEQ ID NO: 25:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: recombinant protein (iii) HYPOTHETICAL: yes (v) FRAGMENT TYPE: internal (vii) IMMEDIATE SOURCE:
          (A) LIBRARY: of recombinant peptides on phage
          (B) CLONE: phagic (ix) FEATURE:
          (A) NAME/KEY: polypeptide
          (B) IDENTIFICATION METHOD: selection with specific antibodies (xi) SEQUENCE DESCRIPTION: SEQ ID NO: 25:

Glu Phe Ser Gly Leu Arg Pro Gly Lys Phe Gln Asp
1               5                  10          12

(2) INFORMATION FOR SEQ ID NO: 26:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 26:

```
Glu Phe Thr Gly Val Arg Glu Ile Ser Phe Gly Asp
1               5                   10      12
```

(2) INFORMATION FOR SEQ ID NO: 27:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 27:

```
Glu Phe Thr Gly Leu Arg Glu Ser Pro Ser Met Asp
1               5                   10      12
```

(2) INFORMATION FOR SEQ ID NO: 28:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 28:

```
Glu Phe Ser His Pro His Phe Ser Gly Leu Glu Asp
1               5               10      12
```

(2) INFORMATION FOR SEQ ID NO: 29:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 29:

```
Glu Phe Thr Gly Leu Arg Ser Arg Tyr Pro Ala Asp
1               5               10      12
```

(2) INFORMATION FOR SEQ ID NO: 30:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 30:

```
Glu Phe Thr Gly Leu Arg His Lys Thr Ser Ala Asp
1               5               10      12
```

(2) INFORMATION FOR SEQ ID NO: 31:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide (B) IDENTIFICATION METHOD: selection with specific antibodies (xi) SEQUENCE DESCRIPTION: SEQ ID NO: 31:

Glu Phe Cys His Pro Leu Ala Pro Ala Gly Thr Phe Cys Gly Asp
1               5                  10                 15

(2) INFORMATION FOR SEQ ID NO: 32:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with
            specific antibodies (xi) SEQUENCE DESCRIPTION: SEQ ID NO: 32:

Glu Phe Cys His Pro Leu Ala Pro Leu Asn Phe Cys Gly Asp
1               5                  10                 14

(2) INFORMATION FOR SEQ ID NO: 33:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with
            specific antibodies (xi) SEQUENCE DESCRIPTION: SEQ ID NO: 33:

Glu Phe Cys Gly His Pro Leu Ala Pro Pro Gln Ala Cys Gly Asp
1               5                  10                 15

(2) INFORMATION FOR SEQ ID NO: 34:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
              (A) LIBRARY: of recombinant peptides on phage
              (B) CLONE: phagic (ix) FEATURE:
              (A) NAME/KEY: polypeptide
              (B) IDENTIFICATION METHOD: selection with specific antibodies (xi) SEQUENCE DESCRIPTION: SEQ ID NO: 34:

Glu Phe Cys His Pro Leu Ser Pro Arg Pro Leu Gln Cys Gly Asp
1               5                   10                  15

(2) INFORMATION FOR SEQ ID NO: 35:

(i) SEQUENCE CHARACTERISTICS:
              (A) LENGTH: 15 amino acids
              (B) TYPE: amino acid
              (C) STRANDEDNESS: single
              (D) TOPOLOGY: linear (ii) MOLECULE TYPE: recombinant protein (iii) HYPOTHETICAL: yes (v) FRAGMENT TYPE: internal (vii) IMMEDIATE SOURCE:
              (A) LIBRARY: of recombinant peptides on phage
              (B) CLONE: phagic (ix) FEATURE:
              (A) NAME/KEY: polypeptide
              (B) IDENTIFICATION METHOD: selection with specific antibodies (xi) SEQUENCE DESCRIPTION: SEQ ID NO: 35:

Glu Phe Cys His Pro Leu Ala Pro Pro His Pro Ser Cys Gly Asp
1               5                   10                  15

(2) INFORMATION FOR SEQ ID NO: 36:

(i) SEQUENCE CHARACTERISTICS:
              (A) LENGTH: 15 amino acids
              (B) TYPE: amino acid
              (C) STRANDEDNESS: single
              (D) TOPOLOGY: linear (ii) MOLECULE TYPE: recombinant protein (iii) HYPOTHETICAL: yes (v) FRAGMENT TYPE: internal (vii) IMMEDIATE SOURCE:
              (A) LIBRARY: of recombinant peptides on phage
              (B) CLONE: phagic (ix) FEATURE:
              (A) NAME/KEY: polypeptide
              (B) IDENTIFICATION METHOD: selection with specific antibodies (xi) SEQUENCE DESCRIPTION: SEQ ID NO: 36:

Glu Phe Cys His Pro Leu Ser Pro His Pro Ser Tyr Cys Gly Asp
1               5                   10                  15

(2) INFORMATION FOR SEQ ID NO: 37:

(i) SEQUENCE CHARACTERISTICS:
              (A) LENGTH: 15 amino acids
              (B) TYPE: amino acid
              (C) STRANDEDNESS: single
              (D) TOPOLOGY: linear (ii) MOLECULE TYPE: recombinant protein (iii) HYPOTHETICAL: yes (v) FRAGMENT TYPE: internal (vii) IMMEDIATE SOURCE:
              (A) LIBRARY: of recombinant peptides on phage
              (B) CLONE: phagic (ix) FEATURE:
              (A) NAME/KEY: polypeptide
              (B) IDENTIFICATION METHOD: selection with specific antibodies (xi) SEQUENCE DESCRIPTION: SEQ ID NO: 37:

Glu Phe Cys His Pro Leu Ala Thr Gly Pro His Leu Cys Gly Asp
1               5                  10                  15

(2) INFORMATION FOR SEQ ID NO: 38:

(i) SEQUENCE CHARACTERISTICS:
              (A) LENGTH: 15 amino acids
              (B) TYPE: amino acid
              (C) STRANDEDNESS: single
              (D) TOPOLOGY: linear (ii) MOLECULE TYPE: recombinant protein (iii) HYPOTHETICAL: yes (v) FRAGMENT TYPE: internal (vii) IMMEDIATE SOURCE:
              (A) LIBRARY: of recombinant peptides on phage
              (B) CLONE: phagic (ix) FEATURE:
              (A) NAME/KEY: polypeptide
              (B) IDENTIFICATION METHOD: selection with specific antibodies (xi) SEQUENCE DESCRIPTION: SEQ ID NO: 38:

Glu Phe Cys His Pro Leu Ala Pro Ser Pro Ala Val Cys Gly Asp
1               5                  10                  15

(2) INFORMATION FOR SEQ ID NO: 39:

(i) SEQUENCE CHARACTERISTICS:
              (A) LENGTH: 15 amino acids
              (B) TYPE: amino acid
              (C) STRANDEDNESS: single
              (D) TOPOLOGY: linear (ii) MOLECULE TYPE: recombinant protein (iii) HYPOTHETICAL: yes (v) FRAGMENT TYPE: internal (vii) IMMEDIATE SOURCE:
              (A) LIBRARY: of recombinant peptides on phage
              (B) CLONE: phagic (ix) FEATURE:
              (A) NAME/KEY: polypeptide
              (B) IDENTIFICATION METHOD: selection with specific antibodies (xi) SEQUENCE DESCRIPTION: SEQ ID NO: 39:

Glu Phe Cys His Pro Leu Pro Pro Ala Ala Thr Phe Cys Gly Asp
1               5                  10                  15

(2) INFORMATION FOR SEQ ID NO: 40:

(i) SEQUENCE CHARACTERISTICS:
              (A) LENGTH: 15 amino acids
              (B) TYPE: amino acid
              (C) STRANDEDNESS: single (D) TOPOLOGY: linear (ii) MOLECULE TYPE: recombinant protein (iii) HYPOTHETICAL: yes (v) FRAGMENT TYPE: internal (vii) IMMEDIATE SOURCE:
             (A) LIBRARY: of recombinant peptides on phage
             (B) CLONE: phagic (ix) FEATURE:
             (A) NAME/KEY: polypeptide
             (B) IDENTIFICATION METHOD: selection with specific antibodies (xi) SEQUENCE DESCRIPTION: SEQ ID NO: 40:

Glu Phe Cys His Pro Leu Ala Pro Val Pro Arg Gln Cys Gly Asp
1               5                  10                  15

(2) INFORMATION FOR SEQ ID NO: 41:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: recombinant protein (iii) HYPOTHETICAL: yes (v) FRAGMENT TYPE: internal (vii) IMMEDIATE SOURCE:
             (A) LIBRARY: of recombinant peptides on phage
             (B) CLONE: phagic (ix) FEATURE:
             (A) NAME/KEY: polypeptide
             (B) IDENTIFICATION METHOD: selection with specific antibodies (xi) SEQUENCE DESCRIPTION: SEQ ID NO: 41:

Glu Phe Cys His Pro Leu Ser Pro Ser Pro Tyr Met Cys Gly Asp
1               5                  10                  15

(2) INFORMATION FOR SEQ ID NO: 42:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: recombinant protein (iii) HYPOTHETICAL: yes (v) FRAGMENT TYPE: internal (vii) IMMEDIATE SOURCE:
             (A) LIBRARY: of recombinant peptides on phage
             (B) CLONE: phagic (ix) FEATURE:
             (A) NAME/KEY: polypeptide
             (B) IDENTIFICATION METHOD: selection with specific antibodies (xi) SEQUENCE DESCRIPTION: SEQ ID NO: 42:

Glu Phe Cys Asn His Pro Leu Ser Pro Ser Gly Ala Cys Gly Asp
1               5                  10                  15

(2) INFORMATION FOR SEQ ID NO: 43:

```
    (i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 43:

Glu Phe Cys His Ala Val Lys Gly Phe Ser Ala Val Cys Gly Asp
1               5                  10                  15

(2) INFORMATION FOR SEQ ID NO: 44:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 44:

Glu Phe Cys His Ala Val Lys Val Gly Asn Pro Ser Cys Gly Asp
1               5                  10                  15

(2) INFORMATION FOR SEQ ID NO: 45:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 45:

Glu Phe Cys His Ala Thr Lys Thr Pro Trp Thr Thr Cys Gly Asp
1               5                  10                  15
```

(2) INFORMATION FOR SEQ ID NO: 46:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 46:

Glu Phe Cys Arg Ala Pro Ser Gly Val Ile Val Gln Cys Gly Asp
1               5                   10                  15

(2) INFORMATION FOR SEQ ID NO: 47:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: recombinant protein (iii) HYPOTHETICAL: yes (v) FRAGMENT TYPE: internal (vii) IMMEDIATE SOURCE:
        (A) LIBRARY: of recombinant peptides on phage
        (B) CLONE: phagic (ix) FEATURE:
        (A) NAME/KEY: polypeptide
        (B) IDENTIFICATION METHOD: selection with specific antibodies (xi) SEQUENCE DESCRIPTION: SEQ ID NO: 47:

Glu Phe Cys Gly Gly Ala Ser Ser Gly Cys Lys Pro Cys Gly Asp
1               5                   10                  15

(2) INFORMATION FOR SEQ ID NO: 48:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 48:

Gly Glu Phe Tyr Thr Pro Thr Trp Met Leu Pro Glu Asp Pro Lys
1               5                   10                  15

(2) INFORMATION FOR SEQ ID NO: 49:

(i) SEQUENCE CHARACTERISTICS:
        (A) LENGTH: 15 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO: 49:

Gly Glu Phe Ser Pro Pro Trp Met Leu Pro Ser Val Asp Pro Lys
1               5                   10                  15

(2) INFORMATION FOR SEQ ID NO: 50:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 50:

Gly Glu Phe Thr Pro Asn Trp Met Leu Gln Asn Leu Asp Pro Lys
1               5                   10                  15

(2) INFORMATION FOR SEQ ID NO: 51:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 51:

Gly Glu Phe Thr Pro Arg Trp Met Leu Ser Arg Glu Asp Pro Lys
1               5                   10                  15

(2) INFORMATION FOR SEQ ID NO: 52:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 52:

Gly Glu Phe Thr Pro Thr Trp Met Leu Ala Arg Trp Asp Pro Lys
1               5                   10                  15

(2) INFORMATION FOR SEQ ID NO: 53:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 53:

Glu Phe Cys Gly Pro Leu Asp Ser Leu Phe Ala Gln Cys Gly Asp
1               5                   10                  15

(2) INFORMATION FOR SEQ ID NO: 54:

(i) SEQUENCE CHARACTERISTICS:
        (A) LENGTH: 15 amino acids
        (B) TYPE: amino acid
        (C) STRANDEDNESS: single -continued

```
        (D) TOPOLOGY: linear (ii) MOLECULE TYPE: protein (xi) SEQUENCE DESCRIPTION: SEQ ID NO: 54:

Glu Phe Cys Gly Pro Ile Ser Ala Leu Phe Ala Ser Cys Gly Asp
1               5                   10                  15

(2) INFORMATION FOR SEQ ID NO: 55:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 55:

Glu Phe Cys Gly Pro Ile His Ala Leu Phe Leu Asp Cys Gly Asp
1               5                   10                  15

(2) INFORMATION FOR SEQ ID NO: 56:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 56:

Glu Phe Cys Gly Pro Ile Ser Ser Leu Phe Gly Asp Cys Gly Asp
1               5                   10                  15

(2) INFORMATION FOR SEQ ID NO: 57:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 57:

Gly Glu Phe Ile Cys His Ser Asp Cys Ala Ala Gly Asp Pro Lys
1               5                   10                  15

(2) INFORMATION FOR SEQ ID NO: 58:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 58:

Gly Glu Phe Ile Cys His Ser Asp Cys Ala Ser Gly Asp Pro Lys
1               5                   10                  15

(2) INFORMATION FOR SEQ ID NO: 59:

(i) SEQUENCE CHARACTERISTICS:
        (A) LENGTH: 15 amino acids
        (B) TYPE: amino acid
        (C) STRANDEDNESS: single
```

(D) TOPOLOGY: linear (ii) MOLECULE TYPE: protein (xi) SEQUENCE DESCRIPTION: SEQ ID NO: 59:

Gly Glu Phe Ile Ala Cys His Ser Asp Cys Gly Ser Asp Pro Lys
1               5                   10                  15

(2) INFORMATION FOR SEQ ID NO: 60:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 60:

Gly Glu Phe Trp Thr Pro Leu Lys Cys Asp Ala Leu Asp Pro Lys
1               5                   10                  15

(2) INFORMATION FOR SEQ ID NO: 61:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 61:

Gly Glu Phe Pro Ala Ala Phe Gly Lys Leu Gly Val Asp Pro Lys
1               5                   10                  15

(2) INFORMATION FOR SEQ ID NO: 62:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 62:

Glu Phe Cys Leu Val Leu Pro Lys Val Lys Met Ala Cys Gly Asp
1               5                   10                  15

(2) INFORMATION FOR SEQ ID NO: 63:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 63:

Glu Phe Cys Ala Arg Leu Pro Val Leu Lys Leu Val Cys Gly Asp
1               5                   10                  15

(2) INFORMATION FOR SEQ ID NO: 64:

(i) SEQUENCE CHARACTERISTICS:
        (A) LENGTH: 15 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO: 64:

Glu Phe Cys Ile Trp Leu Pro Arg Ile Lys Leu Ser Cys Gly Asp
1               5                   10                  15

(2) INFORMATION FOR SEQ ID NO: 65:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 65:

Glu Phe Cys Phe Ser Ile Pro Ser Leu Lys Thr Val Cys Gly Asp
1               5                   10                  15

(2) INFORMATION FOR SEQ ID NO: 66:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 66:

Glu Phe Cys Phe Arg Gly Pro Arg Gln Lys Leu Tyr Cys Gly Asp
1               5                   10                  15

(2) INFORMATION FOR SEQ ID NO: 67:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 67:

Glu Phe Cys Leu Pro Leu Leu Gly Arg Lys Thr Met Cys Gly Asp
1               5                   10                  15

(2) INFORMATION FOR SEQ ID NO: 68:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 68:

Glu Phe Cys Trp Ile His His Leu Leu Lys Val Val Cys Gly Asp
1               5                   10                  15